United States Patent [19]

Benkö et al.

[11] 4,373,100
[45] Feb. 8, 1983

[54] METHYL-QUINOXALINE-1,4-DIOXIDE DERIVATIVES

[75] Inventors: Pal Benkö; Daniel Bozsing; Janos Gundel; Karoly Magyar, all of Budapest, Hungary

[73] Assignee: Egyt Gyogyszervegyeszeti Gyar, Budapest, Hungary

[21] Appl. No.: 269,720

[22] Filed: Jun. 2, 1981

[30] Foreign Application Priority Data

Jun. 3, 1980 [HU] Hungary .................................. 1386

[51] Int. Cl.³ ....................... C09B 23/00; C09B 25/00
[52] U.S. Cl. .................................... 542/439; 542/440; 426/532; 424/250; 544/353
[58] Field of Search ....................... 544/353; 424/250; 426/532; 542/439, 440

[56] References Cited

U.S. PATENT DOCUMENTS 4,303,657 12/1981 You ng et al. ..................... 544/353

FOREIGN PATENT DOCUMENTS 2354252 3/1974 Fed. Rep. of Germany ...... 544/353

Primary Examiner—Paul J. Killos
Attorney, Agent, or Firm—Karl F. Ross

[57] ABSTRACT

The invention relates to fodder additives, fodder concentrates and fodders with weight gain increasing and fodder utilization improving effects, which contain as active agent a new compound of the general formula (I),

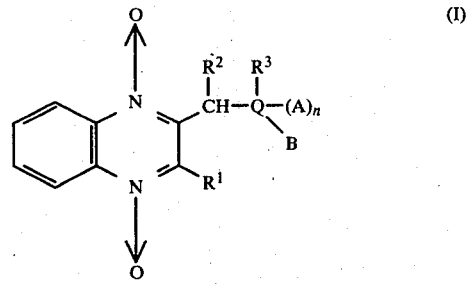

The invention also relates to a process for the preparation of compounds having the general formula (I) by reacting a compound of the general formula (II),

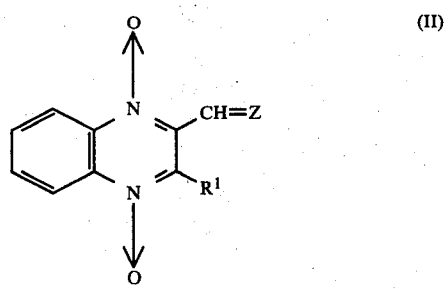

wherein Z is oxygen atom or represents two lower alkoxy groups and $R^1$ is as defined above, with a compound of the general formula (III),

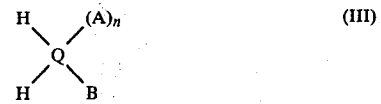

wherein Q, A, B and n are as defined above, and, if desired, converting the resulting compound of the general formula (I) into another compound of the general formula (I) by well-known reactions.

The compounds of the general formula (I) are new.

11 Claims, No Drawings

METHYL-QUINOXALINE-1,4-DIOXIDE DERIVATIVES

The invention relates to new methyl-quinoxaline-1,4-dioxide derivatives, a process for the preparation thereof and compositions - particularly feed additives, fodder concentrates and animal feeds - containing the same.

It is known that certain quinoxaline-1,4-dioxide derivatives possess antimicrobial and weight gain increasing properties. In U.S. Pat. No. 3,371,090 Schiff-bases of 2-formylquinoxaline-1,4-dioxide are disclosed. Other quinoxaline-1,4-dioxide derivatives are described in Belgian Pat. No. 764,088, GFR Pat. No. 1,670,935, U.S. Pat. No. 3,344,022 and DOS No. 2,354,252.

According to the present invention there are provided new methyl-quinoxaline-1,4-dioxide derivatives of the formula (I),

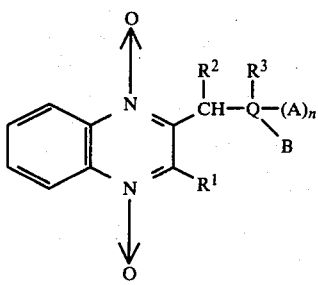

wherein
$R^1$ is hydrogen or lower alkyl,
$R^2$ is hydroxy and
$R^3$ is hydrogen, or
$R^2$ and $R^3$ form together a valence bond,
Q represents a carbon or nitrogen atom,
A is hydrogen, hydroxymethyl, lower alkyl, phenyl-lower alkyl or lower alkoxycarbonyl,
n is 0 or 1,
B is nitro, cyano, halogen, unsubstituted or halogeno- or nitro-substituted phenyl, pyridyl, quinolyl or a group of the formula (IV),

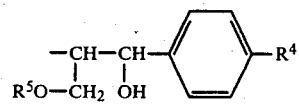

in which
$R^5$ is hydrogen or lower alkylcarbonyl and
$R^4$ stands for nitro, amino, trifluoromethyl, lower alkyl or lower alkoxy, or
A and B, together with the adjacent carbon atom to which they are attached, form a 5- or 6-membered unsubstituted or substituted heterocyclic ring which contains not more than two identical or different nitrogen and/or oxygen and/or sulfur heteroatoms and which can contain one or two exocyclic oxygen atoms and/or sulfur atoms and/or imino groups,
and where Q is a nitrogen atom, n is 0 and B is a group of the formula (IV), and where Q represents a carbon atom, B is other than a group of the formula (IV), and biologically acceptable acid addition salts of the compounds of the formula (I) with basic character.

The compounds of the formula (I) contain one or more asymmetric carbon atoms and thus can exist in the form of racemic mixtures or enantiomers. The invention encompasses all of the possible racemic forms and enantiomers of the compounds having the formula (I).

The term "lower alkyl" refers to straight-chain or branched saturated aliphatic hydrocarbyl groups with 1 to 4 carbon atoms (e.g. methyl, ethyl, n-propyl, isopropyl, and n-butyl). The term "phenyl-lower alkyl" refers to lower alkyl groups with phenyl substituents, such as benzyl, α-phenethyl, β-phenethyl, and β,β-diphenylethyl. The term "lower alkoxy" relates to straight-chain or branched alkylether groups having 1 to 4 carbon atoms, e.g. methoxy, ethoxy and n-propoxy. The "lower alkoxycarbonyl" groups contain the lower alkoxy groups defined above (e.g. methoxycarbonyl or ethoxycarbonyl). The term "halogen" encompasses the fluorine, chlorine, bromine and iodine atoms. The term "lower alkylcarbonyl" relates to acid residues of lower alkanoic acids with 1 to 4 carbon atoms (e.g. acetyl, propionyl or butyryl).

A and B together with the adjacent carbon atom to which they are attached can represent a 5- or 6-membered, substituted or unsubstituted heterocyclic ring containing not more than two identical or different nitrogen and/or oxygen and/or sulfur heteroatoms and optionally one or two oxocyclic oxygen atoms and/or sulfur atoms and/or imino groups. This ring may be 4-oxo-2-thion-5-thiazolidinyl, 2,4-dioxo-5-thiazolidinyl, 4-oxo-2-imino-5-thiazolidinyl, imidazolidinyl, 2,4-dioxo-imidazolidinyl, pyrimidinyl, 4,6-dioxo-2-thion-5-pyrimidinyl, oxazolyl, 5-oxo-2-oxazolyl, or 2-phenyl-5-oxo-4-oxazolyl.

The compounds of the formula (I) with basic character can form acid addition salts. For salt formation suitable inorganic acids (e.g. hydrochloric acid, hydrobromic acid or sulfuric acid or nitric acid, etc.) or organic acids (e.g. lactic acid or malic acid or maleic acid or fumaric acid or tartaric acid) can be used.

$R^1$ is preferably hydrogen.

A and B preferably form, together with the adjacent carbon atom to which they are attached, a thiazolidinyl group which can have one or two exocyclic oxygen and/or sulfur atoms and/or imino groups.

Particularly preferred representatives of the compounds of the formula (I) are the following:
RS-(2-quinoxalinyl-1,4-dioxide)-(4'-oxo-2'-thion-5'-thiazolidinyl)-methanol,
2S-(-)-threo-2-(2'-quinoxalinyl-methylidene-1',4'-dioxide)-amino-1-(p-nitrophenyl)-1,3-propanediol, and
RS-1-hydroxy-1-(2'-quinoxalinyl-1',4'-dioxide)-2-nitropropane.

Further preferred compounds of the formula (I) are those disclosed in the Examples.

A compound of the formula (I) having outstanding properties is the product of Example 7, i.e. the compound of the formula (IX).

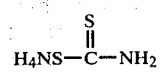

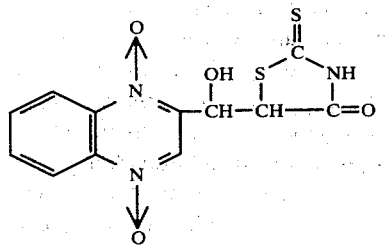

According to a further feature of the invention there is provided a process for the preparation of compounds having the formula (I) and biologically acceptable acid addition salts of the compounds of the formula (I) with basic character, which comprises (a) reacting a compound of the formula (II),

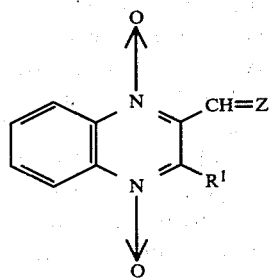

wherein Z represents an oxygen atom or two lower alkoxy groups and $R^1$ is as defined above, with a compound of the formula (III),

wherein Q, A, B and n are as defined above, or (b) oxidizing a compound of the formula (V),

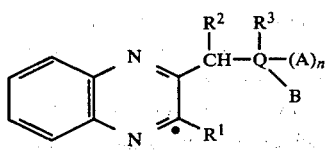

wherein $R^1$, $R^2$, $R^3$, Q, A, B and n are as defined above, or (c) to prepare compounds of the formula (I), wherein $R^2$ is hydroxy, $R^3$ is hydrogen and A and B form, together with the adjacent carbon atom to which they are attached, a 4-oxo-2-thion-5-thiazolidinyl group, reacting a compound of the formula (VI),

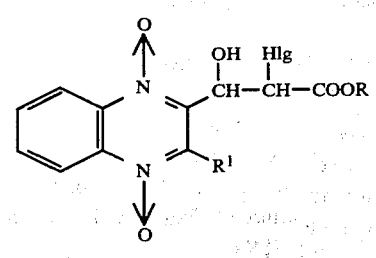

wherein Hlg is halogen, R is lower alkyl and $R^1$ is as defined above, with ammonium dithiocarbamate of the formula (VII), $$H_4NS-\overset{\overset{S}{\|}}{C}-NH_2 \quad (VII)$$

or (d) for the preparation of compounds of the formula (I), wherein $R^2$ and $R^3$ form together a valence bond, dehydrating a compound of the formula (I), in which $R^2$ is hydroxy and $R^3$ is hydrogen, or (e) to prepare compounds of the formula (I), wherein A and B form, together with the adjacent carbon atom to which they are attached, a 5- or 6-membered, optionally substituted heterocyclic ring containing not more than two identical or different nitrogen and/or oxygen and/or sulfur heteroatoms and one or two exocyclic sulfur atoms, reacting a corresponding compound of the formula (I), wherein A and B form, together with the adjacent carbon atom to which they are attached, a 5- or 6-membered, optionally substituted heterocyclic ring containing not more than two identical or different nitrogen and/or oxygen and/or sulfur heteroatoms and one or two exocyclic oxygen atoms and/or imino groups with phosphorous pentasulfide or carbon disulfide, or (f) for the preparation of compounds of the formula (I), wherein $R^5$ is lower alkylcarbonyl, acylating the corresponding compound of the formula (I) in which $R^5$ stands for hydrogen, or (g) for the preparation of compounds of the formula (I), wherein $R^5$ is hydrogen, hydrolyzing the corresponding compound of the formula (I) in which $R^5$ is lower alkylcarbonyl, or (h) for the preparation of compounds of the formula (I), wherein $R^4$ is amino, reducing the corresponding compound of the formula (I) in which $R^4$ is nitro, or (i) for the preparation of compounds of the formula (I), wherein $R^4$ is lower alkoxy, diazotizing the corresponding compound of the formula (I) in which $R^4$ is amino, and reacting the diazonium salt obtained–after or without isolation–with the corresponding lower alkanol, and, if desired, separating a racemic mixture into the enantiomers and/or, if desired, converting a compound of the formula (I) with basic character into a biologically acceptable acid addition salt thereof.

According to method (a) of the invention the reaction of the compounds of the formulae (II) and (III) is performed in an inert solvent, preferably in the presence of a base as catalyst. An excess of one of the reaction partners may also act as solvent. As inert solvent e.g. water, dimethyl formamide, lower alkanols (such as methanol, ethanol, isopropanol, n-butanol, sec.-butanol, or n-hexanol), chlorinated hydrocarbons (e.g. methylene chloride, ethylene chloride, chloroform, or carbon tetrachloride), basic or neutral aromatic or heteroaromatic compounds (e.g. pyridine, quinoline, benzene, toluene, or xylene), aliphatic hydrocarbons (e.g. hexane), aliphatic nitro compounds (e.g. nitromethane, nitroethane, or nitropropane), esters of aliphatic carboxylic acids (e.g. ethyl acetate), secondary and tertiary amines liquid at a temperature of 50° to 80° C. (e.g. piperidine, diethanolamine, triethanolamine, N-methyl-ethanolamine, N,N-dimethyl-ethanolamine, N-methyl-diethanolamine, triisopropylamine, or N,N-dibutyl-ethanolamine)

and mixtures thereof can be used. The proper selection of the solvent to be used lies within the knowledges of one skilled in the art.

In order to enhance the reaction it is preferable to add a basic catalyst to the reaction mixture. For this purpose preferably salts of strong bases formed with weak acids (e.g. sodium acetate), ammonia, primary, secondary or tertiary amines (e.g. n-butylamine, diethylamine, allylamine, triethylamine, benzylamine, ethanolamine, ethylenediamine, 2-amino-heptane, 1-amino-2-propanol, piperidine, or 2-amino-2-ethyl-1,3-propanediol) may be used. Compounds containing at least one primary amino group and a secondary amino group and having a $pK_b$ value between 3 and 5 can be used, too. Furthermore, alkali fluorides, zinc (II) fluoride, basic ion exchange resins of the amine type (e.g. weak basic polystyrene-polyamines, polystyrene resins bearing diethylamino groups, etc.) or alkali hydroxides can be used as a catalyst as well.

The starting substance of the formula (II) can be used in the form of the free aldehyde (Z stands for an oxygen atom) or as a dialkyl acetal (Z stands for two alkoxy groups). The molar ratio of the starting substances of the formulae (II) and (III) is from about 1:1 to about 1:1.5. It is preferred to use the two reactants in approximately equimolar amounts. The amount of the catalyst is of no decisive importance and can vary within wide ranges. The catalyst can be used generally in an amount of about 0.1–100%, preferably about 0.5–30% related to the weight of the starting substance of the formula (II). The reaction can be carried out at a temperature between about 0° C. and about 100° C., preferably between 20° C. and 80° C. The reaction time depends on the reactivity of the starting substances and the reaction temperature and may vary generally between 30 minutes and 8 hours. The reaction may also be carried out under superatmospheric pressures. It is preferred, however, to perform the reaction under atmospheric pressure.

According to method (b) of the invention a compound of the formula (V) is oxidized. The oxidation is performed by methods known per se. One may use preferably a peracid s (e.g. peracetic acid perbenzoic acid m-chloroperbenzoic acid) as the oxidizing agent. The peracid can also be formed directly in the reaction medium from the corresponding carboxylic acid and hydrogen peroxide. The reaction is performed preferably at a temperature of about 10° C. to 80° C. The excess of the aqueous peracid solution may serve as reaction medium as well.

According to method (c) of the invention a compound of the formula (VI) is reacted with ammonium dithiocarbamate of the formula (VII). The reaction is carried out preferably in an aqueous acidic medium, in the presence of an aqueous mineral acid (e.g. hydrochloric acid). According to a preferred embodiment of this process the reaction is started in aqueous medium at room temperature and completed in the presence of a mineral acid under heating.

According to method (d) of the invention an organic solvent or solvent mixture is used as reaction medium. For this purpose preferably aprotic organic solvents (e.g. dimethyl formamide, dimethyl sulfoxide etc.) can be used. Dehydration is carried out preferably in the presence of a protic catalyst, such as aliphatic, aromatic or heteroaromatic carboxylic acids, anhydrides thereof, sulfonic acids or mineral acids. It is preferred to use acetic acid, acetic anhydride, trifluoroacetic acid or trifluoroacetic anhydride as a catalyst. The reaction temperature is of no decisive importance and may vary preferably between 0° C. and 40° C., and more particularly can be room temperature. The hydroxy compounds may be subjected to dehydration without or after isolation.

According to method (e) of the invention an exocyclic oxygen atom or imino group is exchanged for a sulfur atom by methods known per se. The reaction may be carried out with phosphorous pentasulfide or carbon disulfide, but other appropriate sulfurizing agents may be used as well. If carbon disulfide is used the reaction can be carried out preferably at about 140°–180° C. in a closed system. If phosphorous pentasulfide is used the reaction may be accomplished preferably at a temperature range of about 120°–160° C.

According to method (f) of the invention acylation is carried out by methods known per se. The conventional acylating agents can be used, preferably the anhydride, halide (particularly chloride) or the ester of the corresponding acid. The reaction is carried out with heating, preferably at a temperature between 60° C. and the boiling point of the reaction mixture. The reaction medium is preferably an apolar organic solvent (e.g. dimethyl formamide or dimethyl sulfoxide) or an excess of the acylating agent used (e.g. acetic anhydride.

According to method (g) of the invention hydrolysis is carried out by methods known per se. The reaction can be performed either in acidic media by using a mineral acid (e.g. hydrochloric acid, etc.) or in alkaline media with the aid of an alkali hydroxide or lower alkylamine (e.g. methylamine). The reaction can be performed in aqueous or alcoholic medium. The reaction can be accomplished at a temperature between about 35° C. and the boiling point of the reaction mixture.

According to method (h) of the invention reduction can be carried out by methods generally known for the conversion of a nitro group into an amino group. Thus, complex metal hydrides (e.g. sodium borohydride), sodium sulfide or Bechamps reduction (iron and hydrochloric acid or zinc and hydrochloric acid) can be used. The reaction can be carried out at a temperature between about 0° C. and room temperature. The reducing agents and the reaction conditions are to be selected so that the quinoxaline-1,4-dioxide structure remains unaffected.

According to method (i) of the invention an amino group is exchanged for a lower alkoxy group by methods known per se. The diazotization of the amino compound can be carried out with cooling, preferably at a temperature in the range of −5° C. to +5° C., with the aid of an alkali nitrite and a mineral acid. The resulting diazonium salt is then reacted, after or preferably without isolation, with the corresponding alkanol under heating.

A racemic mixture can be separated into the enantiomers by methods known per se. This process can be carried out expediently by using conventional and well-known resolution methods.

The compounds of the formula (I) of a basic character can be converted into their biologically acceptable acid addition salts formed with organic or mineral acids. Salt formation can be performed by reacting the base of the formula (I) with an approximately equimolar amount of the corresponding acid in a suitable solvent.

The starting substances of the formulae (II), (III) and (V) are known compounds or can be prepared by methods known per se. The starting substances of the formula (VI) can be prepared by reacting a compound of the formula (II) with a halogenoacetate of the formula (VIII), $$Hlg-CH_2-COOR \qquad (VIII)$$

wherein Hlg is halogen and R stands for lower alkyl.

The new compounds of the formula (I) and their biologically acceptable acid addition salts can be used in animal husbandry for their weight gain increasing and antibacterial effects.

The new compounds of the invention can be used either locally or in a systemic manner for the prophylaxis or treatment of various bacterial infections. These compounds are active against a wide range of gram-positive or gram-negative bacteria, e.g. against the following microorganisms: Escherichia coli, Salmonella cholerasuis, Staphylococcus aureus, Streptococcus pyogenes, Pasteurella multocida.

The minimum inhibiting concentration of the compounds of the formula (I) against the strains listed above is between 0.5 and 120 γ/ml.

The weight gain increasing effect of the new compounds of the formula (I) is shown in the following test. Pigs are used as test animals. For each dosage groups of 6 animals are used and each experiment with six pigs is repeated three times. The pigs of the test group are fed with a fodder comprising 50 mg/kg of the test compound of the formula (I). The animals in each test group are fed with the same fodder and under identical conditions except for the kind and amount of the test compound incorporated into the fodder. The animals of the control group receive the same fodder but without the test compound of the formula (I). The results obtained are summarized in Table I.

TABLE I

| Test compound (Example No.) | Average daily weight gain, related to the controls | Weight of fodder producing 1 kg of weight gain, related to the controls |
|---|---|---|
| 2 | 137.8% | 87.1% |
| 5 | 129.5% | 86.0% |
| 7 | 150.2% | 72.0% |

It appears from the above data that the weight gain of the animals fed with a fodder containing the compounds of the invention is significantly greater than that of the pigs of the control group. At the same time the same weight gain can be achieved with a considerably smaller amount of fodder when a compound of the formula (I) is incorporated into the animal feed. This is proof of an improved fodder utilization.

An important advantage of the compounds of the invention resides in the fact that they are eliminated from the animal organism within a considerably shorter time than the known quinoxaline-1,4-dioxide derivatives, i.e. their retention time is considerably shorter. This is a significant advantage in animal husbandry.

The toxicity of the compounds of the formula (I) against domestic animals is so low that they practically can be regarded as atoxic.

According to a further feature of the invention there are provided compositions for use in animal husbandry comprising as active ingredient an effective amount of a compound of the formula (I), wherein Q, A, B, n, $R^1$, $R^2$ and $R^3$ are as defined above, or a biologically acceptable acid addition salt of a compound of the formula (I) of basic character in admixture with suitable inert solid or liquid carriers or diluents.

These compositions can be provided in forms generally used in veterinary practice, such as tablets, coated tablets boluses, etc. These compositions may contain the usual inert carriers, diluents and additives and can be prepared by methods well known in the pharmaceutical industry.

The compositions of the present invention may be particularly fodder additives, fodder concentrates and fodders comprising as active ingredient in an effective amount a compound of the formula (I), wherein Q, A, B, n, $R^1$, $R^2$ and $R^3$ are as defined above, or a biologically acceptable acid addition salt of a compound of the formula (I) with basic character in admixture with suitable edible solid or liquid carriers or diluents and additives.

According to a further feature of the invention there is provided a process for the preparation of fodder additives, fodder concentrates and fodders, which comprises admixing a compound of the formula (I), wherein Q, A, B, n, $R^1$, $R^2$ and $R^3$ are as defined above, or a biologically acceptable acid addition salt of a compound of the formula (I) with basic character with a suitable edible solid or liquid carrier or diluent and additive generally used in the production of fodder additives and fodders.

As carrier or diluent any substance of vegetable or animal origin applicable in the feeding of animals or serving as fodder can be used. For this purpose e.g. wheat, rice, maize, soybean, alfalfa, barley, oats, rye can be used in appropriate forms (grit, groats, meal, bran, etc.), furthermore fish meal, meat meal, bone meal or mixtures thereof can be used as well. One may advantageously use a fiber-free green plant fodder concentrate with high protein content (e.g. VEPEX$^R$).

As additives silicic acid, wetting agents, antioxidants, starch, dicalcium phosphate, calcium carbonate, sorbic acid, etc. can be used. As wetting agent non-toxic oils, preferably soybean oil, maize oil or mineral oil can be employed. Various alkylene glycols can also be used as wetting agent. The starch used may be wheat, maize or potato starch.

The fodder additives and concentrates may contain usual vitamins (e.g. vitamin A, $B_1$, $B_2$, $B_3$, $B_6$, $B_{12}$, E, K) and trace elements (e.g. Mn, Fe, Zn, Cu, I), too.

The active ingredient content of the compositions may vary within a wide range. The fodder additives and concentrates may contain about 5–80% by weight, preferably about 10–50% by weight of the active ingredient of the formula (I). The active ingredient content of the animal fodders ready for use may be about 1–400 ppm, preferably about 10–100 ppm.

The fodder additives and concentrates are diluted with suitable fodder components or are incorporated into suitable animal feeds to provide animal feeds ready for use.

The fodders according to the present invention can be used for the increase of weight gain and improvement of feed utilization of various domestic animals, such as pigs, lambs, cattle and poultry, particularly pigs.

Further details of the present invention are to be found in the following Examples without limiting the scope of the invention to the Examples. The melting points disclosed in the Examples were determined on a Koffler apparatus.

EXAMPLE 1

Preparation of
RS-1-hydroxy-1-(2'-quinoxalinyl-1',4'-dioxide)-2-nitroethane 19.0 g (0.1 moles) of 2-formyl-quinoxaline-1,4-dioxide and 0.85 g (0.01 moles) of piperidine are dissolved in 200 ml of isopropanol, and 6.1 g (0.1 moles) of nitromethane are added dropwise to the mixture. The reaction mixture is stirred at 50° C. for 2 hours, thereafter cooled and filtered. 18.8 g (75%) of the named compound are obtained; m.p.: 198°–200° C.

EXAMPLE 2

Preparation of
RS-1-hydroxy-1-(2'-quinoxalinyl-1',4'-dioxide)-2-nitropropane 19.0 g (0.1 moles) of 2-formyl-quinoxaline-1,4-dioxide are reacted with 7.5 g of nitroethane for 2 hours as described in Example 1. The named compound is obtained with a yield of 87% (23 g); m.p.; 196°–197° C.

EXAMPLE 3

Preparation of
RS-1-(2'-quinoxalinyl-1',4'-dioxide)-2-nitro-1,3-propanediol

A mixture of 9.5 g (0.05 moles) of 2-formyl-quinoxaline-1,4-dioxide, 4.55 g (0.05 moles) of 2-nitroethanol, 100 ml of isopropanol and 0.4 g of piperidine is stirred at 40° C. for 4 hours. The reaction mixture is cooled, filtered, and the filtrate is washed with ether. 5 g (36%) of the named compound are obtained; m.p.: 65°–70° C.

EXAMPLE 4

Preparation of
2R-(-)-threo-2-(2'-quinoxalinyl-methylidene-1',4'-dioxide)-amino-1-(p-nitrophenyl)-1,3-propanediol A mixture of 19.0 g (0.1 moles) of 2-formyl-quinoxaline-1,4-dioxide, 21.2 g (0.1 moles) of 2R-(-)-threo-2-amino-1-(p-nitrophenyl)-1,3-propanediol, 250 ml of isopropanol and 4 ml of acetic acid is stirred at 70° C. for 4 hours. The mixture is cooled and filtered. 35.4 g (92%) of the named compound are obtained; m.p.: 176°–178° C., $[\alpha]_D^{20} = +7.03°(c=0.5\%$, in dimethyl sulfoxide).

EXAMPLE 5

Preparation of
2S-(-)-threo-2-(2'-quinoxalinyl-methyl-idene-1',4'-dioxide)-amino-1-(p-nitrophenyl)-1,3-propanediol 19.0 g (0.1 moles) of 2-formyl-quinoxaline-1,4-dioxide are reacted with 21.2 g (0.1 moles) of 2S-(-)-threo-2-amino-1-(p-nitrophenyl)-1,3-propanediol under the conditions given in Example 4. 35.4 g (92%) of the named compound are obtained; m.p.: 192°–193° C., $[\alpha]_D^{20} = -7.03°(c=0.5\%$, in dimethyl sulfoxide).

EXAMPLE 6

Preparation of
2S-(-)-threo-2-(2'-quinoxalinyl-methyl-idene-1',4'-dioxide)-amino-1-(p-nitrophenyl)-3-acetoxypropanol A mixture of 19.2 g (0.05 moles) of 2S-(-)-threo-2-2'-quinoxalinyl-methylidene-1',4'-dioxide)-amino-1-(p-nitrophenyl)-1,3-propanediol and 130 ml of acetic anhydride is boiled for 5 minutes. The reaction mixture is cooled and filtered. 10 g (47%) of the named compound are obtained; m.p.: 266°–268° C., $[\alpha]_D^{20} = -5.50°(c=0.5\%$, in dimethyl sulfoxide).

EXAMPLE 7

Preparation of
RS-(2-quinoxalinyl-1,4-dioxide)-(4'-oxo-2'-thion-5'-thiazolidinyl)-methanol A mixture of 19.0 g (0.1 moles) of 2-formyl-quinoxaline-1,4-dioxide, 13.3 g (0.1 moles) of 4-oxo-thiazolidine-2-thion, 200 ml of isopropanol and 4 ml of a 10% aqueous sodium hydroxide solution is stirred at room temperature for 3 hours. The mixture is cooled and the separated product is filtered off. 30.7 g (95%) of the named compound are obtained; m.p.: 293°–294° C.

EXAMPLE 8

Preparation of
RS-(3-methyl-2-quinoxalinyl-1,4-dioxide)-(4'-oxo-2'-thion-5'-thiazolidinyl)-methanol A mixture of 2.0 g (0.01 moles) of 3-methyl-2-formyl-quinoxaline-1,4-dioxide, 1.33 g (0.01 moles) of 4-oxo-thiazolidine-2-thion, 50 ml of isopropanol and 0.4 ml of a 10% aqueous sodium hydroxide solution is reacted and then processed as described in Example 7. 2.7 g (80%) of the named compound are obtained; m.p.: 213°–215° C.

EXAMPLE 9

Preparation of
RS-(2-quinoxalinyl-1,4-dioxide)-(2',4'-diketo-5'-imidazolidinyl)-methanol A mixture of 9.5 g (0.05 moles) of 2-formyl-quinoxaline-1,4-dioxide, 3.6 (0.05 moles) of 2,4-diketo-imidazolidine, 100 ml of isopropanol and 2 ml of a 10% aqueous sodium hydroxide solution is stirred at 40° C. for 5 hours. The mixture is cooled, the separated product is filtered off and dried. 12.0 g (82.7%) of the named compound are obtained; m.p.: 190° C. (decomposition).

EXAMPLE 10

Preparation of
RS-(α-hydroxy-2-quinoxalinyl-1,4-dioxide)-thiobarbituric acid

A mixture of 19.0 g (0.1 moles) of 2-formyl-quinoxaline-1,4-dioxide, 11.2 g (0.1 moles) of thiobarbituric acid, 180 ml of isopropanol and 0.4 g of piperidine is stirred at 60° C. for 3 hours. The mixture is cooled and the separated product is filtered off. 33 g (98.7%) of the named compound are obtained; m.p.: above 300° C.

EXAMPLE 11

Preparation of
RS-(2-quinoxalinyl-1,4-dioxide)-2'-thion-4'-hydroxy-6'-amino-5'-primidinyl)-methanol 9.5 g (0.05 moles) of 2-formyl-quinoxaline-1,4-dioxide are dissolved in 100 ml of pyridine, and the solution is cooled to 0° C. A mixture of 7.16 g (0.05 moles) 2-thion-4-one-6-imino-pyrimidine and 5 drops of piperidine are added to the mixture, and the solution is stirred for 8 hours at 0°–5° C. The separated crystals are filtered off. 15.8 g (95%) of the named compound are obtained; m.p.: above 350° C.

EXAMPLE 12

Preparation of
E-2-thion-4-hydroxy-6-amino-5-(2'-quinoxalinyl-methylidene-1',4'-dioxide)-pyrimidine A mixture of 3.3 g (0.01 moles) of RS-(2-quinoxalinyl-1,4-dioxide)-(2'-thion-4'-hydroxy-6'-amino-5'-pyrimidinyl)-methanol, 30 ml of dimethyl formamide and 3 drops of trifluoroacetic anhydride is stirred at room temperature for 15 minutes. The reaction mixture is poured into ice-cold water, and the separated product is filtered off. 2.84 g (90%) of the named compound are obtained; m.p.: above 300° C.

EXAMPLE 13

Preparation of
RS-(2-quinoxalinyl-1,4-dioxide)-(2'-phenyl-5'-one-4'-oxazolyl)-methanol A mixture of 19 g (0.1 moles) of 2-formyl-quinoxaline-1,4-dioxide, 16.1 g (0.1 moles) of 2-phenyl-5-oxazolone, 250 ml of isopropanol and 0.85 g (0.01 moles) of piperidine is stirred at 50° C. for 2 hours. The mixture is cooled, and the resulting red suspension is filtered. 21 g (60%) of the named compound are obtained; m.p.: 158°–160° C. (decomposition).

EXAMPLE 14

Preparation of
E-2-phenyl-4-(2'-quinoxalinyl-methylidene-1', 4'-dioxide)-5-oxazolone A mixture of 19 g (0.1 moles) of 2-formyl-quinoxaline-1,4-dioxide, 17.9 g (0.1 moles) of N-benzoyl-glycine, 150 ml of acetic anhydride and 15 g (0.18 moles) of sodium acetate is stirred at 60° C. for one hour. The reaction mixture is cooled, the product is filtered off and washed successively with water and isopropanol. 21.7 g (65%) of the named compound are obtained as red crystals; m.p.: 216°–218° C.

EXAMPLE 15

Preparation of
E-2-phenyl-4-(2'-quinoxalinyl-methyl-idene-1',4'-dioxide)-5-oxazolone A mixture of 3.51 g (0.01 moles) of RS-(2-quinoxalinyl-1,4-dioxide)-(2'-phenyl-5'-one-4'-oxazolyl)-methanol, 10 ml of dimethyl formamide and 3 drops of trifluoroacetic anhydride is stirred at room temperature for 15 minutes. The resulting suspension is cooled and filtered. 3.0 g (90%) of the named compound are obtained; m.p.: 218°–220° C.

EXAMPLE 16

Preparation of
E-2-thion-4-oxo-5-(2'-quinoxalinyl-methylidene-1',4'-dioxide)-thiazolidine 3.23 g (0.01 moles) of RS-2-quinoxalinyl-1,4-dioxide)-(4'-oxo-2'-thion-5'-thiazolidinyl)-methanol are suspended in 16 ml of a 1:1 mixture of dimethyl sulfoxide and dimethyl formamide. The resulting suspension is stirred, and 1 ml of trifluoroacetic anhydride are added to it in small portions. The reaction mixture is stirred at room temperature for 4 hours, the separated solid product is filtered off and washed with ethanol. 2.14 g of the named compound are obtained (yield: 70%); m.p.: 190°–195° C.

EXAMPLE 17

Preparation of
RS-(2-quinoxalinyl-1,4-dioxide)-(4'-oxo-2'-thion-5'-thiazolidinyl)-methanol A mixture of 14.6 ml (0.05 moles) of RS-(2-quinoxalinyl)-(4'-oxo-2'-thion-5'-thiazolidinyl)-methanol and 100 ml of a 12% peracetic acid is stirred at 50° C. for 20 hours. The reaction mixture is neutralized with a 10 N sodium hydroxide solution under cooling and then filtered. 13.1 g (81%) of the named compound are obtained; m.p.: 293°–294° C.

EXAMPLE 18

Preparation of
RS-2-chloro-3-hydroxy-3-(2'-quinoxalinyl-1',4'-dioxide)-propionic acid ethyl ester 9.5 g (0.05 moles) of 2-formyl-quinoxaline-1,4-dioxide and 6.13 g (0.05 moles) of chloroacetic acid ethyl ester are reacted under the conditions described in Example 1. The reaction mixture is evaporated, the product is filtered off and dried. 11.73 g (75%) of the named compound are obtained; m.p.: 205°–206° C.

EXAMPLE 19

Preparation of
RS-(2-quinoxalinyl-1,4-dioxide)-(4'-oxo-2'-thion-5'-thiazolidinyl)-methanol A mixture of 15.6 g (0.05 moles) of RS-2-chloro-3-hydroxy-3-(2'-quinoxalinyl-1',4'-dioxide)-propionic acid ethyl ester, 5.5 g (0.05 moles) of ammonium dithiocarbamate and 50 ml of water is stirred at room temperature for 0.5 hours. The reaction mixture is admixed with 50 ml of 6 n hydrochloric acid, and the resulting mixture is boiled for a short period of time. The mixture is cooled and the product is filtered off. 10.5 g (65%) of the named compound are obtained; m.p.: 293°–294° C.

EXAMPLE 20

Preparation of
2S-(−)-threo-2-(2'-quinoxalinyl-methylidene-1',4'-dioxide)-amino-1-(p-nitrophenyl)-1,3-propanediol A mixture of 21.3 g (0.05 moles) of 2S-(−)-threo-2-(2'-quinoxalinyl-methylidene-1',4'-dioxide)-amino-1-(p-nitrophenyl)-3-acet-oxy-propanol and 200 ml of aqueous methylamine is stirred for one hour at 35°–40° C. The reaction mixture is cooled and the product is filtered off. 15.3 g (80%) of the named compound are obtained; m.p.: 190°–192° C.

EXAMPLE 21

Preparation of
2S-(-)-threo-2-(2'-quinoxalinyl-methylidene-1',4'-dioxide)-amino-1-(p-ethoxyphenyl)-1,3-propanediol 17.7 g (0.05 moles) of 2S-(-)-threo-2-(2'-quinoxalinyl-methylidene-1',4'-dioxide)-amino-1-(p-aminophenyl)-1,3-propanediol are dissolved in 100 ml of 25% hydrochloric acid, and a solution of 8.6 g (0.125 moles) of sodium nitrite in 15 ml of water is added to the mixture dropwise at 5° C. When the addition is complete the mixture is stirred for an additional 0.5 hours, thereafter 20 ml of ethanol are added, and the mixture is stirred at 50° C. for one hour. The mixture is cooled and the product is filtered off. 8.0 g (42%) of the named compound are obtained; m.p.: 220°–221° C.

EXAMPLE 22

Preparation of
RS-(2-quinoxalinyl-1,4-dioxide)-(4'-oxo-2'-imino-5'-thiazolidinyl)-methanol 19.0 g (0.1 moles) of 2-formyl-quinoxaline-1,4-dioxide and 11.6 g (0.1 moles) of 4-oxo-2-imino-thiazolidine are reacted under the conditions described in Example 7. 25.1 g (82%) of the named compound are obtained; m.p.: 220° C.

EXAMPLE 23

Preparation of
RS-(2-quinoxalinyl-1,4-dioxide)-(4'-oxo-2'-thion-5'-thiazolidinyl)-methanol A mixture of 6.1 g (0.02 moles) of RS-(2-quinoxalinyl-1,4-dioxide)-(4'-oxo-2'-imino-5'-thiazolidinyl)-methanol, 1.9 g (0.025 moles) of carbon disulfide and 50 ml of ethanol is heated at 160° C. for 2 hours in a closed vessel. The reaction mixture is cooled and the product is filtered off. 5.5 g (85%) of the named compound are obtained; m.p.: 293°–294° C.

EXAMPLE 24

A premix for supplementing pig fodder is prepared with the following composition:

| Components | Amounts |
|---|---|
| Vitamin A | 3,000,000 IU |
| Vitamin $D_3$ | 600,000 IU |
| Vitamin E | 4,000 IU |
| Vitamin $K_3$ | 400 mg |
| Vitamin $B_1$ | 600 mg |
| Vitamin $B_2$ | 800 mg |
| Vitamin $B_3$ | 2,000 mg |
| Vitamin $B_6$ | 800 mg |
| Vitamin $B_{12}$ | 10 mg |
| Niacine | 4,000 mg |
| Choline chloride | 60,000 mg |
| Active agent according to Example 7 | 10,000 mg |
| Butylhydroxytoluene (antioxidant) | 30,000 mg |
| Flavoring substances | 8,000 mg |
| Sodium saccharate | 30,000 mg |
| Trace elements: | |
| Mn | 8,000 mg |
| Fe | 30,000 mg |
| Zn | 20,000 mg |
| Cu | 6,000 mg |
| I | 100 mg |
| Twice-ground bran ad | 1,000 g |

This premix of vitamins and trace elements is admixed with the basal fodder in a concentration of 0.5 kg per 100 kg.

EXAMPLE 25

A premix for supplementing piglet fodder is prepared with the following composition:

| Components | Amounts |
|---|---|
| Vitamin A | 1,200,000 IU |
| Vitamin $D_3$ | 300,000 IU |
| Vitamin E | 2,000 IU |
| Vitamin $B_2$ | 600 mg |
| Vitamin $B_3$ | 2,000 mg |
| Vitamin $B_{12}$ | 5 mg |
| Niacine | 3,000 mg |
| Choline chloride | 40,000 mg |
| Active agent according to Example 7 | 10,000 mg |
| Butylhydroxytoluene (antioxidant) | 30,000 mg |
| Trace elements: | |
| Mn | 6,000 mg |
| Fe | 10,000 mg |
| Zn | 15,000 mg |
| Cu | 30,000 mg |
| I | 100 mg |
| Twice-ground bran ad | 1,000 g |

This premix of vitamins and trace elements is admixed with the basal fodder in a concentration of 0.5 kg per 100 kg.

EXAMPLE 26

0.5 kg of a premix as described in Example 24 are admixed with 100.0 kg of a basal fodder with the following composition:

| Components | Amounts, kg |
|---|---|
| Maize | 37.6 |
| Barley | 25.4 |
| Wheat | 6.0 |
| Oats | 5.0 |
| Soybean | 13.0 |
| Fish meal | 6.0 |
| Bran | 2.4 |
| Fat powder | 1.5 |
| Premix of minerals* | 1.0 |
| Lime (fodder quality) | 1.0 |
| Sodium chloride | 0.5 |
| Biolisine | 0.1 |
| Premix according to Example 24 | 0.5 |
| Total weight: | 100.0 kg |

The active agent content of the resulting pig fodder is 50 ppm.

*The composition of the premix of minerals is as follows:

| Components | Amounts, % |
|---|---|
| Dicalcium phosphate | 55.0 |
| Monocalcium phosphate | 40.0 |
| Calcium carbonate | 5.0 |

EXAMPLE 27

0.5 kg of a premix as described in Example 25 are admixed with 100.0 kg of a basal fodder with the following composition:

| Components | Amounts, kg |
|---|---|
| Maize | 25.0 |
| Wheat | 34.0 |
| Extracted soybean | 18.0 |
| Milk powder | 9.9 |
| Fish meal | 4.0 |
| Yeast (fodder quality) | 2.0 |
| Fat powder | 3.4 |
| Premix of minerals according to Example 26 | 1.8 |
| Lime (fodder quality) | 1.0 |
| Sodium chloride (fodder quality) | 0.4 |
| Premix according to Example 25 | 0.5 |
| Total weight: | 100.0 kg |

The active agent content of the resulting piglet fodder is 50 ppm.

EXAMPLE 28

400 kg of a pre-ground soybean meal are filled into a mixer, 3.1 kg of soybean oil are added under stirring, and the mixture is stirred until the solids get coated with oil. Thereafter 9.1 kg of an active agent according to Example 7 are added and the mixture is stirred until a homogeneous blend is obtained. Finally 9.0 kg of soybean oil are added, and the mixture is homogenized again.

EXAMPLE 29

0.5 kg of an active agent according to Example 7 are added to 40 kg of corn meal under stirring, and simultaneously 3.0 kg of propylene glycol are sprayed into the mixture. Thereafter 1.4 kg of dicalcium phosphate are added and the mixture is homogenized.

EXAMPLE 30

10 kg of alfalfa meal and 15 kg of VEPEX ® are stirred for 20 minutes, thereafter 1 kg of maize oil is started to spray into the mixture with an even speed so that spraying is continued during the introduction of the following additional components: 2.5 kg of an active agent according to Example 1, 10 kg of maize starch, 2.5 kg of the above active agent, 0.3 kg of silicon dioxide, 0.6 kg of ascorbic acid, 9 kg of maize starch and 2.5 kg of the above active agent. Thereafter the mixture is stirred for an additional 5 minutes.

EXAMPLE 31

One proceeds as described in Example 28 with the difference that butylene glycol is applied as wetting agent instead of soybean oil.

EXAMPLE 32

(A) 3.5 kg of potato starch are admixed with 2.9 kg of an active agent according to Example 2. 0.05 kg of mineral oil are sprayed into the mixture, thereafter 0.2 kg of sorbic acid, 0.4 kg of silicon dioxide and 0.1 kg of calcium propionate are added, and the mixture is stirred for an additional 2 minutes.

(B) 4.2 kg of fish meal are admixed with 22 kg of rye bran, 0.6 kg of mineral oil are sprayed into the mixture, thereafter 4 kg of a mixture prepared according to point (A), 10 kg of maize meal, 4 kg of a mixture prepared according to point (A) and 9 kg of maize meal are introduced under stirring. Finally 0.6 kg of mineral oil are sprayed into the mixture.

EXAMPLE 33

100 kg of wheat bran, 10 kg of an active agent according to Example 5, 2.5 kg of calcium carbonate, 0.15 kg of α-tocopherol and 0.4 kg of calcium propionate are homogenized with 4 kg of propylene glycol.

EXAMPLE 34

10 kg of soybean meal and 0.6 kg of an active agent according to Example 3 are homogenized with 2.5 kg of butylene glycol.

EXAMPLE 35

50 kg of soybean meal, 6 kg of an active agent according to Example 7, 0.5 kg of silicon dioxide and 0.2 kg of calcium propionate are homogenized with 1.6 kg of soybean oil.

We claim:
1. A compound of the formula (Ia)

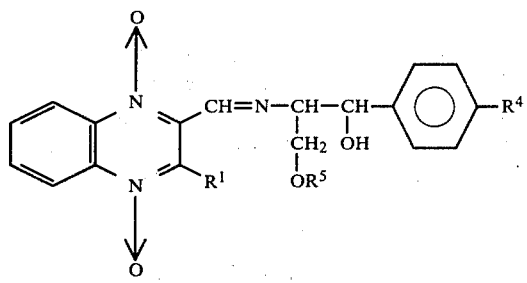

wherein
$R^1$ is hydrogen or lower alkyl;
$R^4$ is nitro, amino, trifluoromethyl, lower alkyl or lower alkoxy; and
$R^5$ is hydrogen or lower alkylcarbonyl; or a pharmaceutically acceptable acid accition salt thereof.

2. The compound defined in claim 1 which is 2R-(−)-threo-2-(2'-quinoxalinyl-methylidene-1',4'-dioxide)-amino-1-(p-nitrophenyl)-1,3-propanediol or a pharmaceutically acceptable acid addition salt thereof.

3. The compound defined in claim 1 which is 2S-(−)-threo-2-(2'-quinoxalinyl-methylidene-1',4'-dioxide)-amino-1-(p-nitrophenyl)-1,3-propanediol or a pharmaceutically acceptable acid addition salt thereof.

4. The compound defined in claim 1 which is 2S-(−)-threo-2-(2'-quinoxalinyl-methylidene-1',4'-dioxide)-amino-1-(p-nitrophenyl)-3-acetoxypropanol or a pharmaceutically acceptable acid addition salt thereof.

5. The compound defined in claim 1 which is 2S-(−)-threo-2-(2'-quinoxalinyl-methylidene-1',4'-dioxide)-amino-1-(p-ethoxyphenyl)-1,3-propanediol or a pharmaceutically acceptable acid addition salt thereof.

6. A compound of the formula (Ib)

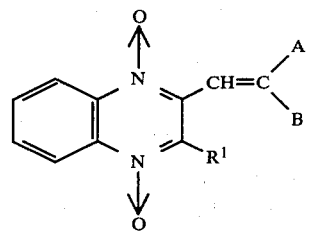

wherein
$R^1$ is hydrogen or lower alkyl; and
A and B together with the adjacent carbon atom to which they are attached forms 4-oxo-2-thion-5-thiazolidinyl, 2,4-dioxo-5-thiazolidinyl, 4-oxo-2-imino-thiazolidinyl, imidazolidinyl, 2,4-dioxo-imidazolidinyl, pyrimidinyl, pyrimidinyl substituted by hydroxy, thiol or amino, oxazolyl, 5-oxo-2-oxazolyl, or 2-phenyl-5-oxo-4-oxazolyl; or a pharmaceutically acceptable acid addition salt thereof.

7. A compound of the formula (Ic)

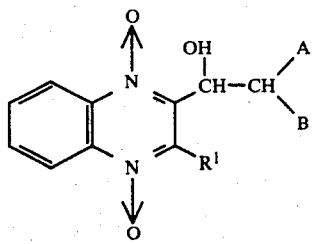

wherein
R[1] is hydrogen or lower alkyl; and
A and B together with the adjacent carbon atom to which they are attached forms 4-oxo-2-thion-5-thiazolidinyl, 2,4-dioxo-5-thiazolidinyl, 4-oxo-2-imino-thiazolidinyl, imidazolidinyl, 2,4-dioxoimidazolidinyl, pyrimidinyl, pyrimidinyl substituted by hydroxy, thiol or amino, oxazolyl, 5-oxo-2-oxazolyl or 2-phenyl-5-oxo-4-oxazolyl; or a pharmaceutically acceptable acid addition salt thereof.

8. The compound defined in claim 7 which is RS-(2-quinoxalinyl-1,4-dioxide-(4'-oxo-2'-thion-5'-thiazolidinyl)-methanol or a pharmaceutically acceptable acid addition salt thereof.

9. A composition for use in animal husbandry comprising as active ingredient an effective amount of a compound as defined in claim 1, claim 6 or claim 7 in admixture with a suitable inert solid or liquid carrier or diluent.

10. A fodder additive, fodder concentrate or fodder having antimicrobial and/or weight gain increasing effects as defined in claim 9, comprising as active ingredient an effective amount of a compound as defined in claim 1, claim 6 or claim 7 in admixture with an edible solid or liquid carrier or diluent.

11. A method for improving the weight gain and fodder utilization of animals, which comprises feeding said animals with a fodder according to claim 10.

* * * * *